US006950693B1

(12) United States Patent
Wehberg

(10) Patent No.: US 6,950,693 B1
(45) Date of Patent: Sep. 27, 2005

(54) DEVICE RECORDING A THERMO-OPTICAL IMAGE OF THE FEMALE BREAST

(76) Inventor: Heinrich Wehberg, Etelserstrasse 32, 27299 Langwedel (DE)

( * ) Notice: Subject to any disclaimer, the term of this patent is extended or adjusted under 35 U.S.C. 154(b) by 0 days.

(21) Appl. No.: 10/018,131

(22) PCT Filed: Apr. 18, 2000

(86) PCT No.: PCT/DE00/01243

§ 371 (c)(1),
(2), (4) Date: Jan. 31, 2002

(87) PCT Pub. No.: WO00/64332

PCT Pub. Date: Nov. 2, 2000

(30) Foreign Application Priority Data

Apr. 22, 1999 (DE) .......................... 299 07 186 U
Jun. 16, 1999 (DE) .............................. 199 27 426

(51) Int. Cl.[7] .............................................. A61B 6/00
(52) U.S. Cl. ..................................................... 600/476
(58) Field of Search ............................... 600/473, 474, 600/475–477, 407

(56) References Cited

U.S. PATENT DOCUMENTS

| | | | |
|---|---|---|---|
| 3,970,074 A | 7/1976 | Mogos et al. ................ 128/2 H |
| 4,055,166 A | 10/1977 | Simpson et al. ............ 128/2 H |
| 4,135,497 A | * 1/1979 | Meyers et al. ............... 600/549 |
| 4,186,748 A | * 2/1980 | Schlager ...................... 600/549 |
| 4,524,779 A | * 6/1985 | Brown, Jr. ................... 600/549 |
| 4,599,738 A | * 7/1986 | Panetta et al. ................ 378/37 |
| 4,616,912 A | * 10/1986 | Johnsen .......................... 396/5 |
| 4,691,712 A | * 9/1987 | Brown, Jr. ................... 600/549 |
| 5,837,197 A | * 11/1998 | Porrazzo et al. .............. 422/61 |
| 5,995,865 A | * 11/1999 | Carioni ....................... 600/474 |

FOREIGN PATENT DOCUMENTS

DE            3020359          12/1981

OTHER PUBLICATIONS

G. Lauth, G. Mühlberger—Atlas der Plattenthermographie, 1976, Herausgeber: CAWO GmbH, Bremen, Germany. Authors examined 10,000 women with LC Thermography (Liquid crystal thermography) from 1972 to 1975 and by excision or fine needle method did find, from 988 cases, 261 carcinomes. More than 100 coloured images show the importance of cooling the breast during examination with a cooling air blower. However, there are no standards to define the degree of cooling and, therefore, it is impossible to gain reproducible images. If one will reach a high sensitivity and specificity it takes a very long time and a great deal of experience to interpret thermographic images.

\* cited by examiner

Primary Examiner—Ali Imam
(74) Attorney, Agent, or Firm—Jon L. Woodard; Edward W. Goebel, Jr.; MacDonald Illig Jones & Britton LLP

(57) ABSTRACT

Apparatus for recording a thermooptical image of the female breast with a casing, a thermooptical foil, a cooling box, a thermostat, an illuminating system, a digital camera, a clamping device, a contact producing device, a timing system and a release mechanism for automatic release of the digital camera.

32 Claims, 3 Drawing Sheets

DEVICE RECORDING A THERMO-OPTICAL IMAGE OF THE FEMALE BREAST

Like a fingerprint, the vascular pattern in the female breast is individual to every woman and under normal conditions, such patterns remain unchanged. Changes in the vascular pattern of a breast may indicate the presence of a mammary carcinoma or other disorder.

Most conventional methods for detecting and diagnosing mammary carcinomas within the framework of preventive medical examinations, most frequently mammography, incorporate the use of x-rays. These methods lead to a very limited radiation exposure for the patient. As a supplement to mammography, thermography can be used to diagnose mammary carcinomas using skin temperature.

The prior art includes various techniques for performing diagnosis of mammary carcinomas. In one group of methods, skin temperatures are directly measured on the breast. Optionally, such measurements can be further processed electronically. WO 79/00594 and U.S. Pat. No. 3,970,074 disclose apparatuses in which the breast is pressed against a plate equipped with temperature sensors arranged in a matrix-like manner to measure skin temperature. The measured data are electronically processed and specific temperature distributions on the skin are used to indicate the presence of a mammary carcinoma. U.S. Pat. No. 4,055,166 disclosures a brassier, which is fitted with individual temperature sensors that monitor skin temperature constantly at corresponding points. Specific changes to the skin temperature indicate the existence of mammary carcinomas.

A second group of thermographic methods include those using plate thermography, such as in the apparatus disclosed by German Patent D.E. 83 26 341 U1. A thermographic plate is pressed onto the female breast, and as a function of temperature, a thermographic coating on the plate assumes different colors. This method renders patterns of vessels optically visible in a thermographic manner, with certain vessel patterns revealing higher levels of heat than other areas. Specific structures or features indicate abnormal changes. The actual diagnostic method of plate thermography is described in greater detail in "Atlas der Plattenthermographie" by G. Lauth and G. Mühlberger. This atlas gives an introduction to physicians inexperienced in plate thermography. However, plate thermography is limited in that successful use requires an experienced and skilled physician. The technique is prone to high rates of error, especially when utilized by an inexperienced physician.

SUMMARY

In accordance with the invention, an apparatus facilitates diagnosis of pathological changes in the female breast using the surprising discovery that, by cooling a thermooptical foil for predetermined duration and then illuminating and recording a thermooptical image of the foil, it is possible to standardize thermooptical images to similar and reproducible recording conditions to permit easy and more reliable diagnosis of pathological changes.

The invention records a thermooptical image of the female breast using a thermooptical foil positioned on a frame, the foil being cooled to a standardized and constant temperature. The thermooptical foil is positioned adjacent a casing that is opaque except for the side facing the breast, and a cooling box is positioned between the casing and foil. The foil is also positioned to contact the breast, and a timer measures a presettable amount of time that passes after the cooling box begins to cool the foil. The cooling box causes a constant temperature to be established throughout the thermooptical foil, allowing for standardized and reproducible recording conditions. An illuminating system illuminates the thermooptical foil from within the casing and a digital camera is used to record image data from the illuminated foil for evaluation and diagnosis. A triggering mechanism is used to operate the digital camera so that the camera makes its photographic recording of the breast at the end of the presettable amount of time that passes after the cooling box begins to cool the foil.

To effect cooling of the thermooptical foil, the cooling box can use a cooling medium fluid such as water supplied by a cooling medium circuit. The cooling medium circuit includes a cooling medium inlet and a cooling medium outlet, with an adjustable thermostat being used to measure the amount of cooling performed and being responsive to the temperature of the cooling medium. The cooling box can be transparent and an antireflection disk can also be positioned between the cooling box and digital camera.

The foil can have an initial position in which it is not in contact with the cooling box. Pins, springs, or other devices can be included to permit surface contact between the foil and cooling box, and a locking device can be included to fix the foil in place after making contact with the cooling box. A clamping device can also be included in the apparatus for clamping the breast against the foil. In some embodiments, a pad can be used in the clamping device to press the breast against the foil and can be variably spaced from the foil.

In some embodiments, the casing, cooling box, and foil can all be mounted on a multi-articulation arm to permit positioning of apparatus components with respect to the patient being examined. The multi-articulation arm can be mounted on an instrument trolley to permit easy handling of the casing and easy transportation of the apparatus.

Some embodiments of the invention include a monitor screen connected to the digital camera to permit the observation of images as they are viewed through the camera. A computer and keyboard can also be included to operate the triggering mechanism and manipulate image data recorded by the digital camera. Various other types of output devices, such as printers and various facilities for storing digital images recorded by the camera, such as diskette and CD-ROM devices, can also be included.

In some embodiments, image evaluating devices connected to the digital camera can permit automatic evaluation of information contained in the recorded image for the existence of a pathological change or for features characteristic of mammary carcinomas. An image evaluating device can also be configured to compare recorded images with earlier images of the same breast or with reference images. In some embodiments, the monitor screen can be subdivided into two windows, one window being used for displaying the present image and the other window being used for displaying an earlier image of the same breast or a reference image.

Those skilled in the art will realize that this invention is capable of embodiments which are different from those shown in that the details of the structure of the recording apparatus disclosed herein can be changed in various manners without departing from the scope of this invention. Accordingly, the drawings and description are to be regarded as illustrative in nature and are not to restrict the scope of the invention. Additionally, the claims are to be regarded as including such equivalent recording apparatuses as do not depart from the nature and scope of this invention.

BRIEF DESCRIPTION OF THE DRAWINGS

For a more complete understanding and appreciation of this invention and many of its advantages, reference will be made to the following Detailed Description of the Preferred Embodiments taken in conjunction with the accompanying drawings.

DETAILED DESCRIPTION OF THE PREFERRED EMBODIMENTS

Figure 1:
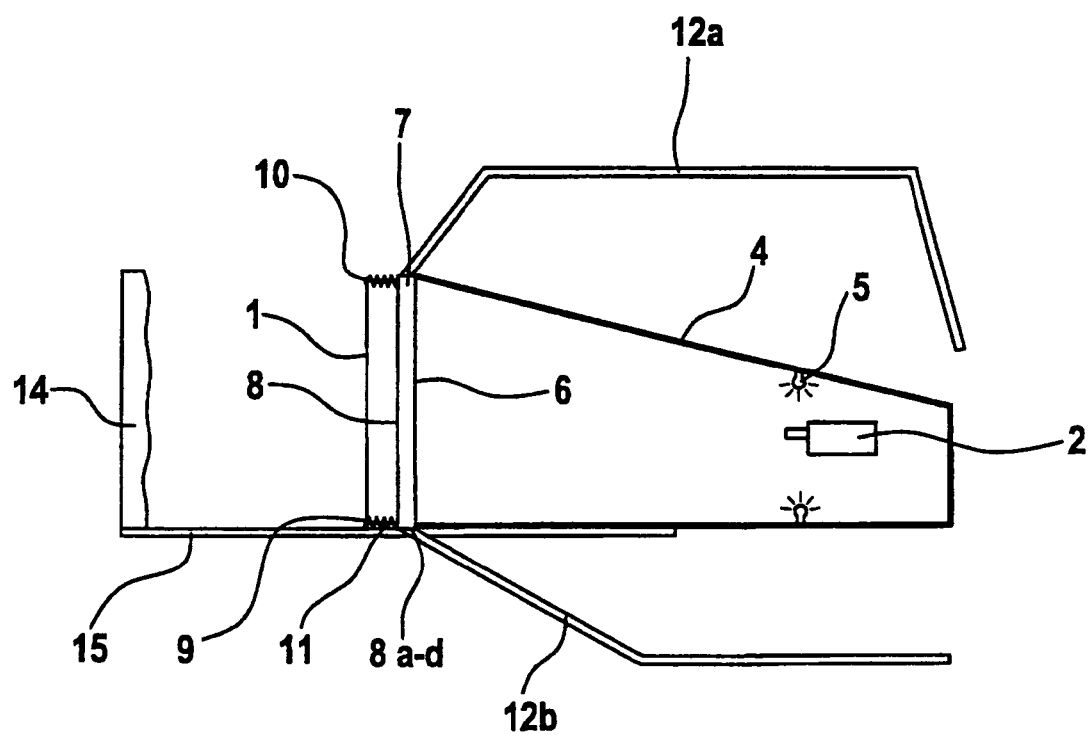
FIG. 1 is a diagrammatic side view of part of one embodiment of an apparatus for recording a thermooptical image of the female breast according to the invention.

Referring now to the drawings, identical reference numerals and letters designate the same or corresponding parts throughout the several figures shown in the drawings.

FIG. 1 diagrammatically depicts a side view of part of a special embodiment of the apparatus according to the invention. The apparatus comprises a casing 4 which, for standardizing the thermooptical images, is opaque except on the side facing the breast where a frame 9 is mounted. This configuration permits image recording to be free from external reflections. A film or thermooptical foil 1 is positioned on the frame 9. A cooler or transparent cooling box 7 and an antireflection disk 6 are placed between the foil 1 and casing 4, with the antireflection disk 6 being placed closer toward the interior of the casing 4 and forming the interior wall of the cooling box 7. The foil 1 can be stretched over the narrow frame 9 and be biased to a relaxed state position (as shown in FIG. 1) that is two to three centimeters in front of a front wall 8 of the cooling box 7. The quadrangular frame 9 is held in the four corners of the casing 4 by steel pins 10 and the spacing of the foil 1 from the front wall of the cooling box 7 is maintained by four springs 11. The springs 11 are inverted over the pins 10 and in the relaxed state are sufficiently long to hold the foil 1 at the relaxed state position away from the front wall 8 of the cooling box 7. The springs 11 and frame 9 are configured so that sufficient spacing exists between the foil 1 and casing 4 to permit adjustments and corrections to the position of the foil 1 after the breast is placed against the foil 1 without creating surface contact between the foil 1 and the front wall 8 of the cooling box 7.

Figure 2:
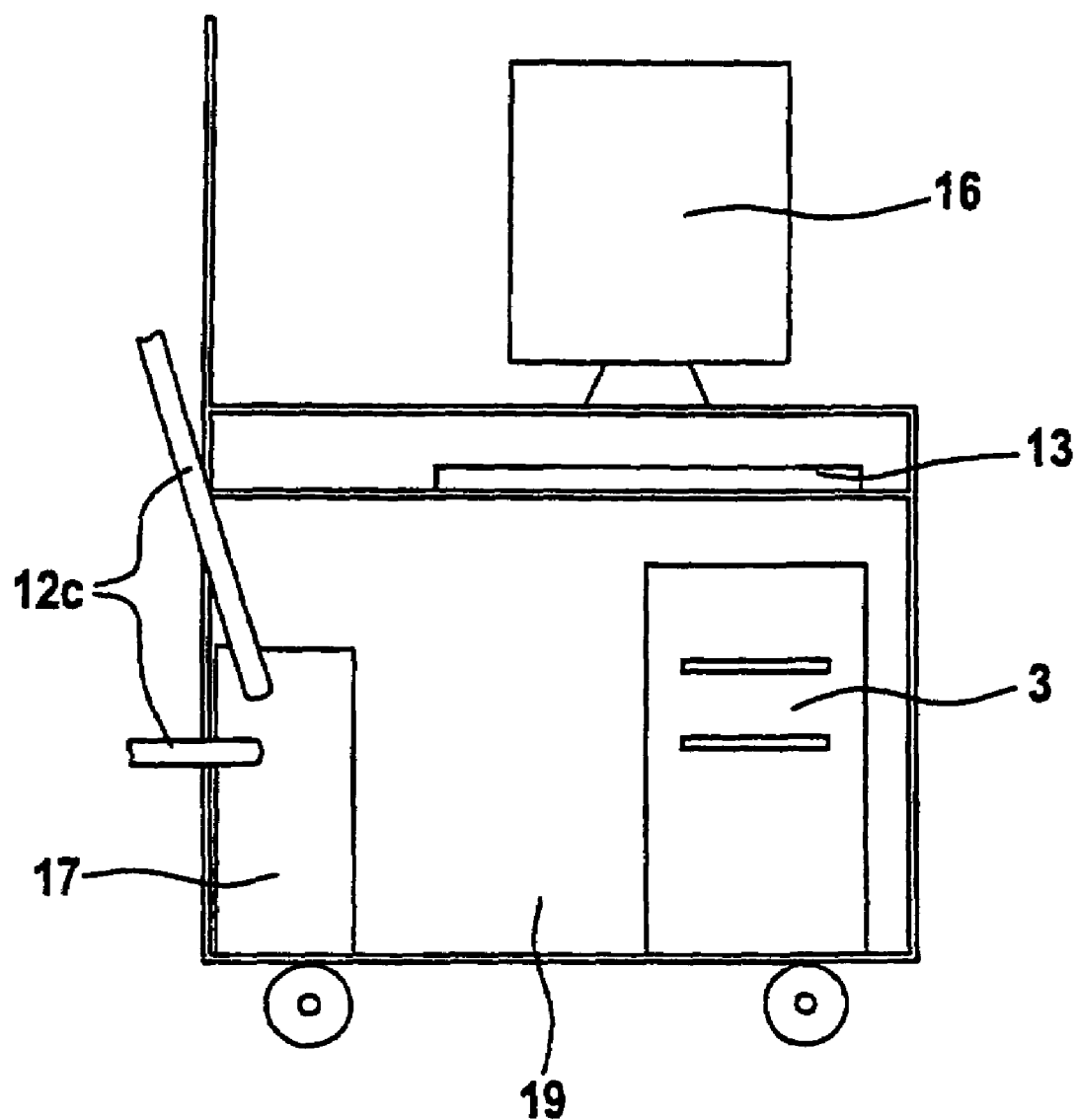
FIG. 2 is another part of the apparatus of FIG. 1.

The cooling box 7 has a cooling medium inlet 12a and a cooling medium outlet 12b connecting the cooling box 7 in a circuit with a thermostat 17 by means of hose lines 12c (cf. FIG. 2). The cooling medium can be a fluid such as water. Continuous water circulation through the cooling medium inlet 12a and cooling medium outlet 12b and constant water temperature ensure the constancy of the temperature of the foil 1. Based on the thermal sensitivity of the foil 1, the set cooling should always be constant. Some embodiments of the invention can allow the operator of the apparatus to perform manual, computer-controlled adjustment of the degree of cooling by the cooling medium, the operator issuing control commands to a computer 3 (cf. FIG. 2) through keyboard 13 (cf. FIG. 2).

A digital camera 2 is positioned inside the casing 4, the digital camera 2 being positioned to record images in the direction of the frame 9. An illuminating system comprises two lamps 5 for illuminating the foil 1, the lamps 5 of the illuminating system being oriented to optimize the recordings of the digital camera 2. In addition, the illumination provided by the lamps 5 contributes to the creation of standardized recording conditions.

A clamping mechanism that includes a pad 14 and mounting support 15 is mounted on the apparatus to gently clamp the breast against the foil 1. As shown in FIG. 1, the mounting support 15 defines a horizontal plane in which the spacing between the pad 14 and foil 1 can be varied by moving the pad 14 along the horizontal plane toward and away from the foil 1. Varying the spacing between the pad 14 and foil 1 enables the breast to be pressed gently but firmly against the foil 1 which further assists in the creation of standardized recording conditions.

Figure 3:
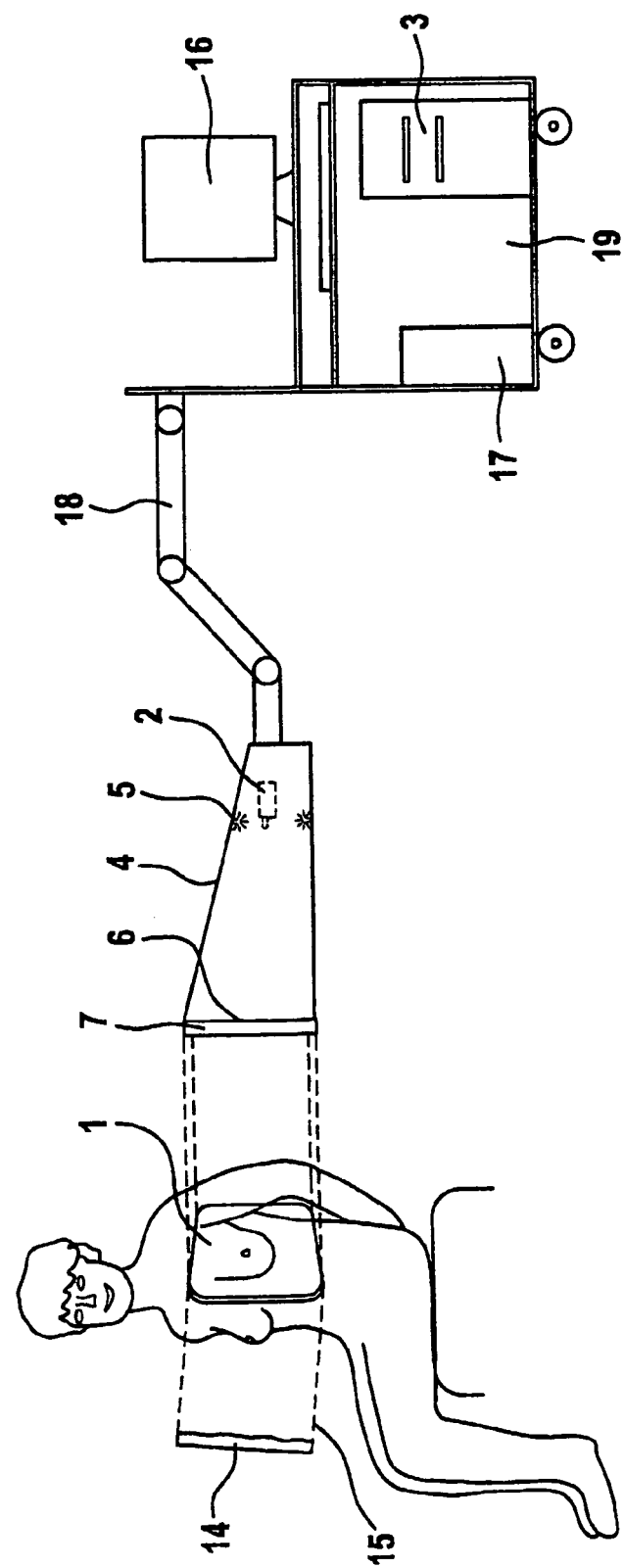
FIG. 3 diagrammatically represents the combined apparatus including the components depicted in FIGS. 1 and 2 as used on a patient.

FIG. 2 diagrammatically depicts another part of the apparatus of FIG. 1. A thermostat 17, a computer 3 with a keyboard 13 and a screen 16 are located in an instrument trolley 19. Referring briefly to FIG. 3, a multi-articulation arm 18 is mounted on the trolley 19, the multi-articulation arm 18 supporting the casing 4 and being extendable to orient the casing 4 into various mobile positions. Some embodiments permit the multi-articulation arm 18 to be locked in order to orient the casing in a fixed position relative to the patient. The multi-articulation arm 18 can also be hollow in order to accommodate power, communication, hosing, and other supply lines to the digital camera 2, cooling box 7, and components of the illuminating system 5.

Referring now to FIG. 3, the connected casing 4 and trolley 19 are represented, the cooling box 7, foil 1, and pad 14 being depicted in an exploded view with the foil 1 being rotated approximately 90° for the purpose of further functional description. The placement of the thermooptical foil 1 on the female breast results in a heat pattern, represented by different colors corresponding to the areal thermal states of the skin, to appear on the foil 1. This thermal pattern is reversible after the foil 1 has been removed from the breast. Cooling the foil 1 has the effect of minimizing coloration of the foil 1, with color patterns becoming more sharply contoured and with contrast to the black background being improved. Cooling the foil has the added effect of reducing the effect that surface or "skin heat" has on the foil coloration, the foil coloration instead displaying and representing peaks of heat dissipated from more low-lying heat sources deep beneath the surface of the breast.

In the operation of the recording apparatus, recording positions correspond to those for mammography, but with the difference that in the case of breasts of normal size, two lateral and two craniocaudal exposures are made for each breast. The reason for this difference is that in "vascugraphy" emitted heat is measured and greater accuracy can be obtained in results by measuring from both sides. After the breast and foil 1 come into contact, the breast is held with the soft pad 14 which the patient can position herself. This is advantageous in that it tends to avoid discomfort associated with the squeezing examination that patients often experience during mammography.

The duration of time in which the foil is cooled is also significant and must be defined and measured in order to establish standardized recording conditions during the cooling process. For example, cooling time can be measured from the instant when the foil 1 is gently pressed counter to the tension of springs 10 on a cooling box 7 and when a locking means (not shown) snaps into a locked position accordingly. At that time, a timing system (not shown) begins to measure the amount of time that passes as the cooling process continues. At the end of a presettable amount of time, the timing system operates a triggering mechanism (not shown) which is used to operate the digital camera 2 to shoot or record the image on the thermooptical foil 1. After completion of the image recording, the pad 14 can be returned to its initial, pre-clamping position to release pressure against the breast. In some embodiments, the releasing action can be provided mechanically with a gas spring pressure mechanism (not shown) incorporated into the mounting support 15. Recording conditions can therefore be standardized by reproducing conditions or "settings" such as the cooling temperature and duration of the cooling period.

During recording or shooting of the thermooptical image by the digital camera 2, all settings can be monitored on the monitor screen 16. The monitor screen further displays all image data being recorded by the digital camera 2. The dimensions of the foil 1 correspond to those of a mammographic film with a size, for example, of 18×24 centimeters. On replacing the foil 1 by a finished mammographic image (e.g. a positive case) and homogeneous transillumination of the film from the outside in the direction of the digital camera 2, it is possible to obtain a simple, inexpensive form of digitized storage of the mammogram for the particular patient. The congruent superimposing of the thermal image and the mammogram on the screen can provide valuable information to the diagnosing doctor. The thermooptical image recorded by the digital camera 2 can then be transferred to the computer 3, where an image evaluation facility can perform an automatic evaluation of the image by utilizing appropriate software. Other types of output devices for storing digital images recorded by the digital camera 16 are also contemplated to be within the scope of the invention and include but are not limited to printed output devices, diskettes, and CD-ROM devices.

The invention can allow for automatic or electronic interpretation of thermooptical images without necessarily requiring the interpretation skills of an examining physician. Pathological changes can be detected by comparing the thermographically obtained vascular pattern and shape of the patient's vessels with reference data, as is particularly appropriate during the initial examinations of a particular patient. However, if previous recordings or exposures exist, it is also possible to carry out a comparison of the current recorded image with one or more images recorded previously. The invention may include a facility for displaying a current recorded image next to a previous recorded image in a split-window fashion. Changes in the thermooptical image may indicate changes in the vascular pattern of the breast which in turn may indicate a pathological change warranting further investigation with another more intrusive diagnostic technique such as a biopsy.

Many other modifications and changes can be made to the recording device of this invention by those skilled in the art without departing from the spirit and scope of this invention. Thus, the claims when appended are intended to be interpreted to cover such equivalent recording apparatuses as do not depart from the spirit and scope of this invention.

What is claimed is:

1. An apparatus for recording a thermooptical image of a female breast on a thermooptical foil comprising:

a casing having a non-opaque side, said non-opaque side being positioned to face a location for the breast when the thermooptical image is recorded;

a thermooptical foil for producing a thermooptical image of the breast having at least first and second surfaces and being positioned between said casing and the location for the breast, said first surface of said thermooptical foil facing said non-opaque side of said casing, said second surface of said thermooptical foil being positioned to contact the breast;

a transparent cooling apparatus which can contact and cool said thermooptical foil to a constant temperature for a presettable amount of time when said thermooptical foil is in contact with the breast; and a camera mounted to record from within said casing the thermooptical image of the foil against the breast at the end of the presettable amount of time.

2. The apparatus for recording a thermooptical image of a female breast of claim 1 further comprising an illuminating system for illuminating said thermooptical foil within said casing.

3. The apparatus for recording a thermooptical image of a female breast of claim 1, said cooling apparatus being configured to cool said thermooptical foil to a constant temperature to allow for standardized and reproducible recording conditions.

4. An apparatus for recording a thermooptical image of a female breast comprising:

a casing having at least one opaque side and a non-opaque side, said non-opaque side being positioned to face a location for the breast when the image is recorded;

a thermooptical foil for producing a thermooptical image of the breast having at least first and second surfaces and being positioned on a frame located between said casing and the location for the breast, said first surface of said thermooptical foil facing said non-opaque side of said casing, said second surface of said thermooptical foil being positioned to contact the breast;

a cooling box mounted adjacent said first surface of said thermooptical foil for cooling said thermooptical foil to a standard temperature at a time when said thermooptical foil contacts the breast;

a timer for measuring a presettable amount of time that passes after said thermooptical foil begins to be cooled by said cooling box;

an illuminating system for illuminating said thermooptical foil within said casing; and a digital camera positioned to record the thermooptical image of the breast on said thermooptical foil from within said casing after the presettable amount of time passes.

5. The apparatus for recording a thermooptical image of claim 4 further comprising a cooling medium circuit for providing a cooling medium to effect cooling of said cooling box, said cooling medium circuit comprising:

a cooling medium inlet for supplying said cooling medium to said cooling box;

a cooling medium outlet for removing said cooling medium from said cooling box; and a thermostat for measuring the amount of cooling performed by said cooling medium circuit, said thermostat being responsive with respect to the temperature of said cooling medium.

6. The apparatus for recording a thermooptical image of claim 4 further comprising an antireflection disk positioned between said thermooptical foil and said digital camera.

7. The apparatus for recording a thermooptical image of claim 4, said thermooptical foil having a relaxed position, said thermooptical foil does not come into contact with said cooling box when in the relaxed position.

8. The apparatus for recording a thermooptical image of claim 4, said frame having a relaxed position and being springingly connected to said casing with at least one mounting device, each said at least one mounting device comprising:

a steel pin extending from said frame to said casing; and a spring having an unloaded condition and an unloaded length and being inverted over said steel pin, said spring extending from said frame to said casing, wherein said spring assumes said unloaded length when assuming said unloaded condition, said unloaded length of said spring being sufficient to maintain a spacial clearance between said cooling box and said thermooptical foil.

9. The apparatus for recording a thermooptical image of claim 8, compression of each said spring permits said frame to assume a non-relaxed position and further permits contact between said thermooptical foil and said cooling box.

10. The apparatus for recording a thermooptical image of claim 4 further comprising a clamping device having a pad for pressing the breast against said thermooptical foil.

11. The apparatus for recording a thermooptical image of claim 4 further comprising a clamping device for clamping the breast against said thermooptical foil, said clamping device comprising:
 a pad for pressing the breast against said thermooptical foil; and
 a mounting support for providing support for said pad and for providing pressure for said pad against said breast.

12. The apparatus for recording a thermooptical image of claim 4 further comprising a clamping device comprising:
 a pad for pressing the breast against said thermooptical foil; and
 a mounting support connected to said casing, said mounting support extending parallel to said frame for providing support for said pad, the spacing between said pad and said thermooptical foil being variable.

13. The apparatus for recording a thermooptical image of claim 4 having a clamping device comprising:
 a pad for pressing the breast against said thermooptical foil, said pad having a major planar pressing surface; and
 a mounting support having a major horizontal dimension and being connected to said casing, said mounting support providing support for said pad, the spacing between said pad and said thermooptical foil being variable, said major planar pressing surface of said pad positioned at about a right angle to said major horizontal dimension of said mounting support.

14. The apparatus for recording a thermooptical image of claim 4 further comprising:
 said frame having a relaxed position, a substantially quadrangular shape, first, second, third and fourth corners, and being springingly connected to said casing with one steel pin in each said corner of said frame, each said steel pin extending from said frame to said casing;
 each said steel pin having a spring, each said spring having an unloaded condition and an unloaded length and being inverted over said pin, each said spring extending from said frame to said casing wherein said spring assumes said unloaded length when assuming said unloaded condition, said unloaded length of said spring being sufficient to maintain a spacial clearance between said cooling box and said thermooptical foil.

15. The apparatus for recording a thermooptical image of claim 14, compression of said springs permits said frame to assume a non-relaxed position and further permits contact between said thermooptical foil and said cooling box.

16. The apparatus for recording a thermooptical image of claim 4, said casing being positioned on a multi-articulation arm to permit variable positioning of said casing.

17. The apparatus for recording a thermooptical image of claim 4, said casing being positioned on a multi-articulation arm mounted on an instrument trolley to permit variable positioning of said casing with respect to said instrument trolley.

18. The apparatus for recording a thermooptical image of claim 4 further comprising a monitor screen connected to said digital camera for monitoring images recorded with said digital camera.

19. The apparatus for recording a thermooptical image of claim 4 further comprising a computer for processing images collected with said digital camera.

20. The apparatus for recording a thermooptical image of claim 4 further comprising a computer for operating said apparatus and for processing information collected with said digital camera.

21. The apparatus for recording a thermooptical image of claim 4 further comprising an information storage medium for storing digital images recorded with said digital camera.

22. The apparatus for recording a thermooptical image of claim 4 further comprising printer output device for producing digital images recorded with said digital camera in a printed format.

23. The apparatus for recording a thermooptical image of claim 4 further comprising an image evaluating device connected to said digital camera for automatic evaluation of information contained in images recorded with said digital camera in response to pathological changes.

24. The apparatus for recording a thermooptical image of claim 4 further comprising an image evaluating device connected to said digital camera for comparing information contained in images recorded with said digital camera to reference images.

25. The apparatus for recording a thermooptical image of claim 4 further comprising an image evaluating device connected to said digital camera for comparing an image recorded by said digital camera for structures or features characteristic of mammary carcinomas.

26. The apparatus for recording a thermooptical image of claim 4 further comprising a monitor screen, said monitor screen being subdivided into first and second windows, said first window configured to display the image recorded by said digital camera, said second image configured to display a reference image for comparison to said first window.

27. An apparatus for recording a thermooptical image of a female breast comprising:
 a casing having at least one opaque side and a non-opaque side, said non-opaque side being positioned to face a location for the breast when the image is recorded;
 a thermooptical foil for producing a thermooptical image of the breast having at least first and second surfaces and being positioned on a frame located between said casing and the location for the breast, said first surface of said thermooptical foil facing said non-opaque side of said casing, said second surface of said thermooptical foil being positioned to contact the breast;
 said frame having a relaxed position, a substantially quadrangular shape, first, second, third and fourth corners, and being springingly connected to said casing with one steel pin in each said corner of said frame, each said steel pin extending from said frame to said casing and having a spring, each said spring having an unloaded condition and an unloaded length and being inverted over said pin, each said spring extending from said frame to said casing wherein said spring assumes said unloaded length;

when assuming said unloaded condition, said unloaded length of said spring being sufficient to maintain a spatial clearance between said cooling box and said thermooptical foil, compression of said springs permits said frame to assume a nonrelaxed position and further permits contact between said thermooptical foil and said cooling box;

a clamping device for clamping the breast against said thermooptical foil, said clamping device having a pad for pressing the breast against said thermooptical foil and a mounting support for providing support for said pad and for providing pressure for said pad against said breast;

a cooling box mounted adjacent said first surface of said thermooptical foil for cooling said thermooptical foil to a standard temperature at a time when said thermooptical foil contacts the breast;

a cooling medium circuit for providing a cooling medium to effect cooling of said cooling box, said cooling medium circuit having a cooling medium inlet for supplying said cooling medium to said cooling box, a cooling medium outlet for removing said cooing medium from said cooling box, and a thermostat for measuring the amount of cooling performed by said cooling medium circuit, said thermostat being responsive to the temperature of said cooling medium;

a timer for measuring a presettable amount of time that passes after said thermooptical foil begins to be cooled by said cooling box;

an illuminating system for illuminating said thermooptical foil within said casing; and a digital camera positioned to record the thermooptical image of the breast on said thermooptical foil from within said casing after the presettable amount of time passes; and an antireflection disk positioned between said thermooptical foil and said digital camera.

28. An apparatus for recording a thermooptical image of a female breast comprising:

a casing having at least one opaque side and a non-opaque side, said non-opaque side being positioned to face a location for the breast when the image is recorded, said casing being positioned on a multi-articulation arm mounted on an instrument trolley to permit variable positioning of said casing with respect to said instrument trolley;

a thermooptical foil for producing a thermooptical image of the breast having at least first and second surfaces and being positioned on a frame located between said casing and the location for the breast, said first surface of said thermooptical foil facing said non-opaque side of said casing, said second surface of said thermooptical foil being positioned to contact the breast;

said frame having a relaxed position, a substantially quadrangular shape, first, second, third and fourth corners, and being springingly connected to said casing with one steel pin in each said corner of said frame, each said steel pin extending from said frame to said casing and having a spring, each said spring having an unloaded condition and an unloaded length and being inverted over said pin, each said spring extending from said frame to said casing wherein said spring assumes said unloaded length when assuming said unloaded condition, said unloaded length of said spring being sufficient to maintain a spacial clearance between said cooling box and said thermooptical foil, compression of said springs permits said frame to assume a nonrelaxed position and further permits contact between said thermooptical foil and said cooling box;

a clamping device for clamping the breast against said thermooptical foil, said clamping device having a pad for pressing the breast against said thermooptical foil and a mounting support for providing support for said pad and for providing pressure for said pad against said breast;

a cooling box mounted adjacent said first surface of said thermooptical foil for cooling said thermooptical foil to a standard temperature at a time when said thermooptical foil contacts the breast;

a cooling medium circuit for providing a cooling medium to effect cooling of said cooling box, said cooling medium circuit having a cooling medium inlet for supplying said cooling medium to said cooling box, a cooling medium outlet for removing said cooing medium from said cooling box, and a thermostat for measuring the amount of cooling performed by said cooling medium circuit, said thermostat being responsive to the temperature of said cooling medium;

a timer for measuring a presettable amount of time that passes after said thermooptical foil begins to be cooled by said cooling box;

an illuminating system for illuminating said thermooptical foil within said casing; and a digital camera positioned to record the thermooptical image of the breast on said thermooptical foil from within said casing after the presettable amount of time passes;

an antireflection disk positioned between said thermooptical foil and said digital camera;

a monitor screen connected to said digital camera for monitoring images recorded with said digital camera; and a computer for operating said apparatus and for processing information collected with said digital camera.

29. A method of recording a thermooptical image of a female breast on a thermooptical foil comprising:

positioning the thermooptical foil against a breast;

cooling the thermooptical foil to a constant temperature for a presettable amount of time while the thermooptical foil is against the breast; and recording a thermooptical image of the foil against the breast at the end of the presettable amount of time.

30. The method of claim 29 which includes recording the thermooptical image from within a casing which is opaque except for a side facing the thermooptical foil and illuminating the thermooptical foil at the time of recording the thermooptical image.

31. The method of claim 29 in which the thermooptical image recorded is examined for pathological changes in the breast.

32. The method of claim 29 in which the thermooptical image recorded is compared to a previously recorded thermooptical image for comparison and evaluation of pathological changes.

* * * * *